United States Patent
Mohammadi

[11] Patent Number: 6,039,935
[45] Date of Patent: Mar. 21, 2000

[54] SUNSCREEN COMPOSITIONS

[75] Inventor: Fatemeh Mohammadi, Hebron, Conn.

[73] Assignee: Elizabeth Arden Company, Division of Conopco, Inc., New York, N.Y.

[21] Appl. No.: 09/251,666

[22] Filed: Feb. 17, 1999

Related U.S. Application Data

[60] Provisional application No. 60/114,199, Dec. 30, 1998.

[51] Int. Cl.[7] .......................... A61K 7/42; A61K 31/74; A61K 7/00
[52] U.S. Cl. .......................... 424/59; 424/60; 424/78.02; 424/400; 424/401
[58] Field of Search .......................... 424/59, 60, 78.02, 424/400, 401

[56] References Cited

U.S. PATENT DOCUMENTS

| | | | |
|---|---|---|---|
| 4,742,142 | 5/1988 | Shimizu et al. | 428/15 |
| 4,919,934 | 4/1990 | Deckner et al. | 424/401 |
| 4,983,418 | 1/1991 | Murphy et al. | 424/47 |
| 5,008,100 | 4/1991 | Zecchino et al. | 424/59 |
| 5,219,558 | 6/1993 | Woodin, Jr. et al. | 424/59 |
| 5,266,321 | 11/1993 | Shukuzaki et al. | 424/401 |
| 5,362,482 | 11/1994 | Yoneyama et al. | 424/69 |
| 5,412,004 | 5/1995 | Tachibana et al. | 524/27 |
| 5,599,533 | 2/1997 | Stepniewski et al. | 424/78.02 |
| 5,654,362 | 8/1997 | Schulz, Jr. et al. | 524/862 |
| 5,738,841 | 4/1998 | Mellul et al. | 424/59 |
| 5,811,110 | 9/1998 | Granger et al. | 424/401 |
| 5,833,973 | 11/1998 | Dobkowski et al. | 424/78.08 |

FOREIGN PATENT DOCUMENTS

| | | |
|---|---|---|
| 97/32561 | 9/1997 | WIPO . |
| 97/44010 | 11/1997 | WIPO . |
| 98/00103 | 1/1998 | WIPO . |
| 98/00105 | 1/1998 | WIPO . |
| 98/18849 | 5/1998 | WIPO . |
| 98/35649 | 8/1998 | WIPO . |
| 99/13859 | 3/1999 | WIPO . |

OTHER PUBLICATIONS

Copy of Estee Lauder *Resilience Lift Face and Throat Crème SPF* 15 carton—1998.

*Primary Examiner*—Shelley A. Dodson
*Attorney, Agent, or Firm*—Milton L. Honig

[57] ABSTRACT

A cosmetic sunscreen composition is provided which includes at least one organic sunscreen, a crosslinked non-emulsifying siloxane elastomer, a volatile siloxane and water. The composition is an oil-in-water emulsion to provide an aesthetically pleasing light skinfeel and rich viscosity, even in the presence of greater than 25% sunscreen oils.

9 Claims, No Drawings

SUNSCREEN COMPOSITIONS

This application claims the benefit of Provisional Application Ser. No. 60/114,199, filed Dec. 30, 1998.

BACKGROUND OF THE INVENTION

1. Field of the Invention

The invention relates to sunscreen compositions, particularly those in lotion and cream form.

2. The Related Art

Sunscreen compositions are commonly used during outdoor work or leisure for protection of exposed skin against sunburn, cancer and even photo aging. Many effective sunscreen preparations are sold commercially or are described in cosmetic or pharmaceutical literature. In general, sunscreen preparations are formulated as creams, lotions or oils containing as the active agent an ultraviolet radiation absorbing chemical compound. The active agent functions by blocking passage of erythematogenic radiation thereby preventing its penetration into the skin.

The ideal sunscreen formulation should be non-toxic and non-irritating to skin tissue and be capable of convenient application in a uniform continuous film. The product should be sufficiently chemically and physically stable so as to provide an acceptable shelf life upon storage. It is particularly desirable that the preparation should retain its protective effect over a prolonged period after application. Thus, the active agent when present on the skin must be resistant to chemical or photodegradation, to absorption through the skin, and to easy removal. For aesthetic reasons, the product should be substantially odorless (or be capable of being scented) and be non-staining to the skin or clothing.

Sunscreen agents in the order of decreasing effectiveness may be categorized as either highly chromophoric monomeric organic compounds, inorganic compounds and minimally chromophoric polymeric organic solids.

U.S. Pat. No. 5,219,558 (Woodin, Jr. et al.) and U.S. Pat. No. 4,919,934 (Deckner et al.) disclose photoprotection compositions wherein the active sunscreen agents are of the chromophoric monomeric organic compound variety. The examples feature the commercially common sunscreens such as octyl methoxycinnamate (Parsol MCX), benzophenone-3 (Oxybenzone) and octyl dimethyl PABA.

Typical of prestige cosmetic sunscreens is a product from Estee Lauder sold under the trademark "Resilience Lift Face and Throat Creme SPF 15". Octyl methoxycinnamate and titanium dioxide are the active sunscreen agents formulated in a base including water, Polysilicone-11, cyclomethicone, emulsifiers and a variety of other minor ingredients. Much of this technology is reported in U.S. Pat. No. 5,599,533 (Stepniewski et al.) which focuses upon water-in-oil emulsions containing organopolysiloxane elastomers.

Chromophoric monomeric organic compounds are subject to certain problems. One of the more important problems is that of skin irritation. These compounds when present on the skin must be resistant to removal by perspiration, skin oils or water. Formulations containing these materials therefore require additives to ensure substantivity. Yet even with the best additives, waterproofing and rub-off resistance is never fully accomplished. Therefore, it would be quite desirable to minimize the levels of such compounds in any sunscreen compositions. Total replacement of chromophoric organic compounds, while desirable, is presently not feasible for high SPF compositions that also require certain types of aesthetics.

Inorganic particulate compounds such as titanium dioxide have been employed as sunscreen agents. In fact, titanium dioxide is quite popular with marketers advertising them as "natural sunscreens". The problem with inorganic particulate compounds is that high SPF values can only be achieved with high concentrations of these materials. Unfortunately, aesthetics suffer at such high concentrations. Clear formulas become opaque. High loadings also tend to form visible white films on the skin which consumers perceive negatively.

Polymeric organic particulates are a final category of materials which have found use in sunscreen formulations. U.S. Pat. No. 5,008,100 (Zecchino et al.) reports oil-in-water emulsions containing polyethylene particles as a co-active sunscreen agent along with the traditional chromophoric organic compounds. Similar to the inorganic materials, polymeric particles are limited in their sunscreen effectiveness. High amounts of such materials will have adverse effects upon the formula aesthetics.

Accordingly, it is an object of the present invention to provide a sunscreen composition that maximizes the sun protection factor but minimizes the level of chromophoric monomeric organic compound.

Another object of the present invention is to provide a sunscreen composition in the form of an oil and water emulsion that exhibits improved aesthetics when applied to the skin.

Still another object of the present invention is to provide a sunscreen composition in the form of an oil and water emulsion that exhibits a good skinfeel and maintains adequate viscosity.

These and other objects of the present invention will more readily become apparent from the description and examples which follow.

SUMMARY OF THE INVENTION

A cosmetic sunscreen composition is provided which includes:

(i) from about 0.1 to about 40% by weight of an organic sunscreen agent with a chromophoric group active within the ultraviolet radiation range from 290 to 400 nm;

(ii) from about 1 to about 90% by weight of water;

(iii) from about 0.05 to about 10% of a crosslinked non-emulsifying siloxane elastomer;

(iv) from about 10 to about 80% of a volatile siloxane; and wherein the composition is an oil-in-water emulsion.

DETAILED DESCRIPTION OF THE INVENTION

Now it has been discovered that exceptional aesthetics (e.g. light skinfeel), stability and rich viscosity (non-watery) properties are achieved by combination of an organic sunscreen, a crosslinked non-emulsifying siloxane elastomer and a volatile siloxane. Of particular importance is that the system be an oil-in-water emulsion rather than a water-in-oil type.

A first essential element of the present invention is that of a sunscreen agent. The agent should have at least one chromophoric group absorbing within the ultraviolet range somewhere from 290 to 400 nm. Chromophoric organic sunscreen agents may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, alpha-phenyl cinnamonitrile; butyl cinnamoyl pyruvate); Dihydroxycinnamic acid derivatives (umbelliferone, methylumbelliferone, methylacetoumbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naptholsulfonates (sodium salts of 2-naphthol-3,6-disulfonic and of 2-naphthol-6,8-disulfonic acids); Dihydroxy-naphthoic acid and its salts; o- and p-Hydroxydiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy-or-methoxy-substituted benzophenones; Uric and vilouric acids; Tannic acid and its derivatives; Hydroquinone; Benzophenones (Oxybenzone, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone, 4-isopropyldibenzoylmethane, Butylmethoxydibenzoylmethane, Etocrylene, and 4-isopropyl-dibenzoylmethane).

Particularly useful are: 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)] aminobenzoate, 2-ethylhexyl-2-cyano-3,3-diphenylacrylate, 2-ethylhexylsalicylate, glycerol p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl-5-sulfoniobenzoxazoic acid and mixtures thereof.

Suitable commercially available organic sunscreen agents are those identified under the following table.

TABLE I

| CTFA NAME | TRADE NAME | SUPPLIER |
| --- | --- | --- |
| Benzophenone-3 | UVINUL M-40 | BASF Chemical Co. |
| Benzophenone-4 | UVINUL MS-40 | BASF Chemical Co. |
| Benzophenone-8 | SPECTRA-SORB UV-24 | American Cyanamid |
| DEA-Methoxycinnamate | BERNEL HYDRO | Bernel Chemical |
| Ethyl dihydroxypropyl-PABA | AMERSCREEN P | Amerchol Corp. |
| Glyceryl PABA | NIPA G.M.P.A. | Nipa Labs. |
| Homosalate | KEMESTER HMS | Humko Chemical |
| Menthyl anthranilate | SUNAROME UVA | Felton Worldwide |
| Octocrylene | UVINUL N-539 | BASF Chemical Co. |
| Octyl dimethyl PABA | AMERSCOL | Amerchol Corp. |
| Octyl methoxycinnamate | PARSOL MCX | Bernel Chemical |
| PABA | PABA | National Starch |
| 2-Phenylbenzimidazole-5-sulphonic acid | EUSOLEX 6300 | EM Industries |
| TEA salicylate | SUNAROME W | Felton Worldwide |
| 2-(4-Methylbenzildene)-camphor | EUSOLEX 6300 | EM Industries |
| Benzophenone-1 | UVINUL 400 | BASF Chemical Co. |
| Benzophenone-2 | UVINUL D-50 | BASF Chemical Co. |

TABLE I-continued

| CTFA NAME | TRADE NAME | SUPPLIER |
| --- | --- | --- |
| Benzophenone-6 | UVINUL D-49 | BASF Chemical Co. |
| Benzophenone-12 | UVINUL 408 | BASF Chemical Co. |
| 4-Isopropyl dibenzoyl methane | EUSOLEX 8020 | EM Industries |
| Butyl Methoxy dibenzoyl methane | PARSOL 1789 | Givaudan Corp. |
| Etocrylene | UVINUL N-35 | BASF Chemical Co. |

Amounts of the aforementioned sunscreen agents will generally range from about 1 to about 45%, preferably from about 20 to about 38%, optimally from about 25 to about 35% by weight.

Crosslinked non-emulsifying siloxane elastomers are a second essential element of this invention. They will have an average number molecular weight in excess of 2,000, preferably in excess of 1,000,000 and optimally will range from about 10,000 to about 20 million. The term "non-emulsifying" defines a siloxane from which polyoxyalkylene units are absent. Advantageously the elastomers are formed from a divinyl compound, particularly a polymer with at least two free vinyl groups, reacting with Si—H linkages of a polysiloxane backbone such as a molecularly spherical MQ resin. Elastomer compositions are commercially available from the General Electric Company under product designation General Electric Silicone 1229 and SFE 839 with proposed CTFA name of Cyclomethicone and Vinyl Dimethicone/Methicone Cross Polymer, delivered as 20–35% and 5–10% respectively in each product of elastomer in a cyclomethicone carrier. A related elastomer composition under the CTFA name of Cyclopentasiloxane and Polysilicone-11 are available as Gransil SR-CYC (7.0+/−20/% elastomer in cyclomethicone) from Grant Industries, Inc., Elmwood Park, N.J. The commercial products from General Electric and Grant Industries ordinarily are further processed by subjecting them to a high pressure (approximately 5,000 psi) treatment in a Sonolator with recycling in 10 to 60 passes. Sonolation achieves a resultant fluid with elastomer average particle size ranging from about 0.01 to about 100 micron, preferably 1 to 30 micron. Viscosity of the resultant fluid is best when ranging between about 300 to about 20,000 cps at 25° C. as measured by a Brookfield LV Viscometer (size 4 bar, 60 rpm, 15 sec.).

Amounts of the crosslinked non-emulsifying siloxane elastomer (without cyclomethicone carrier) should range from about 0.01 to about 10%, preferably from about 0.1 to about 2%, optimally from about 0.5 to about 1% by weight of the cosmetic sunscreen composition. While relatively high concentrations of elastomer provide improved skinfeel properties, too high concentrations result in reduced viscosity of the formulated sunscreen composition. Aesthetically suitable viscosities of the formulated sunscreen compositions as measured on a Brookfield RVF Viscometer (spindle no. 3, 10 rpm at 25° C.) may range from about 1,000 to about 200,000, preferably from about 1,500 to about 30,000, optimally from about 2,000 to about 15,000 cps.

A third essential element of the present invention is that of a volatile siloxane. The term "volatile" refers to those materials having a measurable pressure at ambient conditions. Volatile polyorganosiloxanes useful herein may be cyclic or linear. Preferred cyclic silicones include polydimethylsiloxanes containing from about 3 to about 9 silicon atoms, preferably containing from about 4 to about 5 silicon atoms, generally known as cyclomethicones. Preferred linear silicone oils include the polydimethylsiloxanes containing from about 3 to about 9 silicon atoms. The linear volatile silicones generally have viscosities of less than about 5 centistokes at 25° C., while the cyclic materials have viscosities of less than about 10 centistokes, the preferable range being from about 0.1 to about 8 centistokes. Examples of silicone oils useful in the present invention include: Dow Corning 244, Dow Corning 245, Dow Corning 344, Dow Corning 345 and Dow Corning 200 (manufactured by the Dow Corning Corporation); Silicone 7207 and Silicone 7158 (manufactured by the Union Carbide Corporation); SF 1202 (manufactured by General Electric).

Amounts of the volatile siloxane will range from about 10 to about 80%, preferably from about 20 to about 70%, optimally from about 30 to about 65% by weight.

Compositions of the present inventions will contain water at levels ranging from about 1 to about 90%, preferably from about 10 to about 75%, more preferably from about 20 to about 50%, optimally from about 30 to about 45% by weight.

Surfactants will be a further component of compositions according to the present invention. These may be selected from nonionic, anionic, cationic or amphoteric emulsifying agents. They may range in amount anywhere from about 0.1 to about 20% by weight. Illustrative surfactants, especially those for oil-in-water emulsions are cetyl phosphate available under the trademark Amphisol A®, manufactured by the Givaudan Corporation which can be used in combination with silicone copolyols such as Abil EM 97®, available from the Goldschmidt Company. Other suitable surfactants include Brij 72® (Steareth-2) in combination with Brij 72® (Steareth-21) both from the ICI Corporation.

Compositions of the invention may optionally contain one or more skin conditioning agents. These agents may be selected from humectants, exfoliants or emollients.

Humectants are polyhydric alcohols intended for moisturizing, reducing scaling and stimulating removal of built-up scale from the skin. Typical polyhydric alcohols include polyalkylene glycols and more preferably alkylene polyols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, glycerin, ethoxylated glycerin, propoxylated glycerin and mixtures thereof. Most preferably the humectant is glycerin. Amounts of humectant may range anywhere from about 1 to about 50%, preferably from about 10 to about 40%, optimally from about 25 to 35% by weight.

Exfoliants according to the present invention may be selected from alpha-hydroxycarboxylic acids, beta-hydroxycarboxylic acids and salts of these acids. Most preferred are glycolic, lactic and salicylic acids and their alkali metal or ammonium salts.

When the conditioning agent is an emollient it may be selected from hydrocarbons, fatty acids, fatty alcohols and esters. Petrolatum is the most preferred hydrocarbon type of emollient conditioning agent. Other hydrocarbons that may be employed include mineral oil, polyolefins such as polydecene, and paraffins such as isohexadecane (e.g. Permethyl 99® and Permethyl 101®).

Fatty acids and alcohols will have from 10 to 30 carbon atoms. Illustrative of this category are pelargonic, lauric, myristic, palmitic, stearic, isostearic, hydroxystearic, oleic, linoleic, ricinoleic, arachidic, behenic and euricic acids and alcohols.

Oily ester emollients may be those selected from one or more of the following classes:

1. Triglyceride esters such as vegetable and animal fats and oils. Examples include castor oil, cocoa butter, safflower oil, cottonseed oil, corn oil, olive oil, cod liver oil, almond oil, avocado oil, palm oil, sesame oil, squalene, Kikui oil and soybean oil.
2. Acetoglyceride esters, such as acetylated monoglycerides.
3. Ethoxylated glycerides, such as ethoxylated glyceryl monostearate.
4. Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.
5. Alkenyl esters of fatty acids having 10 to 20 carbon atoms. Examples thereof include oleyl myristate, oleyl stearate, and oleyl oleate.
6. Ether-esters such as fatty acid esters of ethoxylated fatty alcohols.
7. Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters are satisfactory polyhydric alcohol esters.
8. Wax esters such as beeswax, spermaceti, myristyl myristate, stearyl stearate.

Amounts of the skin conditioning agent may range from about 1 to about 50%, preferably from about 3 to about 25%, optimally from about 5 to about 20% by weight.

Waterproofing agents may also be included in compositions of this invention. They may be present at levels from about 0.01 to about 10% by weight. Illustrative is PVP/Eicosene copolymer.

Thickening agents such as Carbomers, CMC gums, xanthan gum and combinations of these may be employed for compositions of this invention. Particularly preferred are Carbomers such as Carbopol 1382® available from the B.F. Goodrich Company. These thickeners are crosslinked acrylic polymers. Amounts of thickener (solids basis without water) may range from about 0.001 to about 5%, preferably from about 0.01 to about 1%, optimally from about 0.1 to about 0.5% by weight.

Minor adjunct ingredients may also be includes such as preservatives, fragrances, antifoam agents, opacifiers and colorants, each in their effective amounts to accomplish their respective functions.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise indicated.

EXAMPLES 1–8

The following formulations are typical of cosmetic sunscreen compositions according to the present invention.

TABLE II

| INGREDIENT | 1 | 2 | 3 | 4 | 5 | 6 | 7 | 8 |
|---|---|---|---|---|---|---|---|---|
| Phase A | | | | | | | | |
| Deionized Water | 21.0 | 17.0 | 15.0 | 13.0 | 11.0 | 22.0 | 15.0 | 19.0 |
| Carbopol 1382 ® (2% Active In Water) | 20.0 | 20.0 | 20.0 | 20.0 | 20.0 | 20.0 | 20.0 | 20.0 |
| EDTA Disodium | 0.10 | 0.10 | 0.10 | 0.10 | 0.10 | 0.10 | 0.10 | 0.10 |
| Butylene Glycol | 1.67 | 1.67 | 1.67 | 1.67 | 1.67 | 1.67 | 1.67 | 1.67 |
| Glycerin | 1.94 | 1.94 | 1.94 | 1.94 | 1.94 | 1.94 | 1.94 | 1.94 |
| Allantoin | 0.20 | 0.20 | 0.20 | 0.20 | 0.20 | 0.20 | 0.20 | 0.20 |
| Phase B | | | | | | | | |
| Amilon ® (nylon, silica and lauryl lysine) | 0.50 | 0.50 | 0.50 | 0.50 | 0.50 | 0.50 | 0.50 | 0.50 |
| Butyl Octyl Salicylate | 5.00 | 5.00 | 5.00 | 5.00 | 5.00 | 5.00 | 5.00 | 5.00 |
| Elefac I-205 ® | 3.00 | 3.00 | 3.00 | 3.00 | 3.00 | 3.00 | 7.00 | 3.00 |
| Benzophenone-3 | 4.00 | 4.00 | 4.00 | 4.00 | 4.00 | 4.00 | 4.00 | 4.00 |
| Homosalate | 6.00 | 6.00 | 6.00 | 6.00 | 6.00 | 6.00 | 6.00 | 6.00 |
| Octocrylene | 1.50 | 1.50 | 1.50 | 1.50 | 1.50 | 1.50 | 1.50 | 1.50 |
| Octyl Methoxycinnamate | 7.50 | 7.50 | 7.50 | 7.50 | 7.50 | 7.50 | 7.50 | 7.50 |
| Octyl Salicylate | 5.00 | 5.00 | 5.00 | 5.00 | 5.00 | 5.00 | 5.00 | 5.00 |
| Phenonip | 0.60 | 0.60 | 0.60 | 0.60 | 0.60 | 0.60 | 0.60 | 0.60 |
| Tocopheryl Acetate | 0.50 | 0.50 | 0.50 | 0.50 | 0.50 | 0.50 | 0.50 | 0.50 |
| Retinyl Linoleate | 0.10 | 0.10 | 0.10 | 0.10 | 0.10 | 0.10 | 0.10 | 0.10 |
| Glycerol Monostearate | 1.00 | 1.00 | 1.00 | 1.00 | 1.00 | 1.00 | 1.00 | 1.00 |
| Cetyl Alcohol | 0.50 | 0.50 | 0.50 | 0.50 | 0.50 | 0.50 | 0.50 | 0.50 |
| PVP/Eicosene Copolymer | 2.00 | 2.00 | 2.00 | 2.00 | 2.00 | 2.00 | 2.00 | 2.00 |
| Amphisol A ® | 2.00 | 2.00 | 2.00 | 2.00 | 2.00 | 2.00 | 2.00 | 2.00 |
| Parsol 1789 ® | 3.00 | 3.00 | 3.00 | 3.00 | 3.00 | 3.00 | 3.00 | 3.00 |
| Phase C | | | | | | | | |
| Polymethylmethacrylate | 2.00 | 2.00 | 2.00 | 2.00 | 2.00 | 2.00 | 2.00 | 2.00 |
| Phase D | | | | | | | | |
| Abil EM 97 ® | 1.00 | 1.00 | 1.00 | 1.00 | 1.00 | 1.00 | 1.00 | 1.00 |
| Gransil SR-5CYC | 2.00 | 6.00 | 8.00 | 10.00 | 12.00 | 1.00 | 4.00 | 4.00 |
| Cyclomethicone (DC 345) | 2.00 | 2.00 | 2.00 | 2.00 | 2.00 | 2.00 | 2.00 | 2.00 |
| Fragrance | 0.15 | 0.15 | 0.15 | 0.15 | 0.15 | 0.15 | 0.15 | 0.15 |
| Phase E | | | | | | | | |
| Deionized Water | 1.83 | 1.83 | 1.83 | 1.83 | 1.83 | 1.83 | 1.83 | 1.83 |
| Potassium Hydroxide (45% solution) | 1.30 | 1.30 | 1.30 | 1.30 | 1.30 | 1.30 | 1.30 | 1.30 |
| DL-Panthenol | 0.20 | 0.20 | 0.20 | 0.20 | 0.20 | 0.20 | 0.20 | 0.20 |
| Phase F | | | | | | | | |
| Actiglide (Special) ® | 0.40 | 0.40 | 0.40 | 0.40 | 0.40 | 0.40 | 0.40 | 0.40 |
| Oat Extract | 2.00 | 2.00 | 2.00 | 2.00 | 2.00 | 2.00 | 2.00 | 2.00 |
| Ergothioneine | 0.10 | 0.10 | 0.10 | 0.10 | 0.10 | 0.10 | 0.10 | 0.10 |

EXAMPLE 9

This Example evaluates the effect of emulsion type and relationship of percent elastomer to viscosity of the final cosmetic product. Table III sets forth the base formulation for a water-in-oil emulsion according to the prior art. Table IV sets forth the base formulation for a oil-in-water emulsion according to the present invention. Comparative viscosity results are listed in Table V.

TABLE III

Water-in-Oil Type Emulsion

| INGREDIENT | WEIGHT % |
|---|---|
| Phase A | |
| Deionized Water | 54.14 |
| Disodium EDTA | 0.10 |
| Glycerin | 1.50 |
| Sodium Chloride | 3.00 |
| Butylene Glycol | 2.50 |
| Phase B | |
| Octymethoxycinnamate | 7.50 |
| Octyl Salicylate | 5.00 |
| Phenonip | 0.60 |
| Vitamin E Acetate | 0.50 |
| Retenyl Linoleate | 0.01 |
| Aluminum Stearate | 5.00 |
| Dow Corning 5225C (Cyclomethicone/Dimethicone Copolyol) | 10.00 |
| Cetyl Dimethicone | 1.00 |
| DC 345 (Cyclomethicone) | 2.00 |
| Elastomer | * |
| ABIL-EM 97 ® | 1.00 |
| Fragrance | 0.15 |

TABLE IV

Oil-In-Water Type Emulsion

| INGREDIENT | WEIGHT % |
|---|---|
| Phase A | |
| Deionized Water | 35.51 |
| Disodium EDTA | 0.10 |
| Glycerin | 1.50 |
| Carbopol 1382 ® (2% solids) | 20.00 |
| Butylene Glycol | 2.50 |
| Phase B | |
| Octymethoxycinnamate | 7.50 |
| Octyl Salicylate | 5.00 |
| Cetyl Dimethicone | 1.00 |
| Phenonip | 0.60 |
| Vitamin E Acetate | 0.50 |
| Retenyl Linoleate | 0.01 |
| Glyceryl Stearate | 1.00 |

TABLE IV-continued

Oil-In-Water Type Emulsion

| INGREDIENT | WEIGHT % |
| --- | --- |
| Cetyl Alcohol | 0.50 |
| Amphisol A ® | 2.00 |
| Octyl Methoxycinnamate | 6.00 |
| Phase C | |
| DC 345 (Cyclomethicone) | 2.00 |
| Elastomer | * |
| ABIL-EM 97 ® | 1.00 |
| Fragrance | 0.15 |
| Phase D | |
| Deionized Water | 1.83 |
| KOH 45% | 1.30 |
| Phase E | |
| Herbal Extract | 2.00 |

TABLE V

Effective Emulsion Type And Elastomer Concentration

| TYPE OF EMULSION | ELASTOMER (% SOLIDS) | VISCOSITY (cps)** | SPF |
| --- | --- | --- | --- |
| Water-In-Oil | 0.6 | 7600 | 14.6 |
| Water-In-Oil | 0.75 | 2000 | 15.2 |
| Water-In-Oil | 1.125 | 800 | 14.8 |
| Oil-In-Water | 0.6 | 19000 | 12.8 |
| Oil-In-Water | 0.75 | 16000 | 13.6 |
| Oil-In-Water | 1.125 | 23000 | 13.1 |

**Brookfield RVF Viscometer: W/O measured with Spindle No. 3 at 10 rpm at 25° C. O/W measured with Spindle TC at 10 rpm at 25° C.

Evident from Table V is that the viscosities of the oil continuous phase emulsions resulted in substantially lower, poorer viscosities than those achieved with the water continuous phase emulsions. In fact, viscosity decreases as the amount of elastomer increases in the water-in-oil type emulsion compositions.

The foregoing description and examples illustrate selected embodiments of the present invention. In light thereof variations and modifications will be suggested to one skilled in the art, all of which are within the spirit and purview of this invention.

What is claimed is:

1. A cosmetic sunscreen composition comprising:
   (i) from about 0.1 to about 40% by weight of an organic sunscreen agent with a chromophoric group active within the ultraviolet radiation range from 290 to 400 nm;
   (ii) from about 1 to about 90% by weight of water;
   (iii) from about 0.05 to about 10% of a crosslinked non-emulsifying siloxane elastomer;
   (iv) from about 10 to about 80% of a volatile siloxane; and
   wherein the composition is an oil-in-water emulsion.

2. The composition according to claim 1 wherein the crosslinked non-emulsifying siloxane elastomer is formed from a divinyl compound reacting with Si-H linkages of a polysiloxane.

3. The composition according to claim 1 further comprising from about 1 to about 50% of a skin conditioning agent selected from the group consisting of humectants, exfoliants, emollients and mixtures thereof.

4. The composition according to claim 1 further comprising from 0.001 to 2% by weight of a crosslinked acrylic polymer.

5. The composition according to claim 4 wherein the polymer is a Carbomer.

6. The composition according to claim 1 wherein the organic sunscreen is selected from the group consisting of benzophenone-3, homosalate, butylmethoxydibenzoylmethane, octyl methoxycinnamate, octylsalicylate and combinations thereof.

7. The composition according to claim 1 wherein the organic sunscreen agent is at least one agent with total amount ranging from about 12 to about 20% by weight.

8. The composition according to claim 7 comprising three organic sunscreen agents.

9. The composition according to claim 1 wherein the elastomer is present in an amount from about 0.1 to about 2% by weight.

* * * * *